United States Patent [19]

Yeboah

[11] 4,382,145

[45] May 3, 1983

[54] METHOD OF HYDROLYZING ORGANOCHLOROSILANES

[75] Inventor: Yaw D. Yeboah, Scotia, N.Y.

[73] Assignee: General Electric Company, Schenectady, N.Y.

[21] Appl. No.: 298,663

[22] Filed: Sep. 2, 1981

[51] Int. Cl.³ .............................................. C07F 7/08
[52] U.S. Cl. ................................. 556/460; 556/452; 556/461
[58] Field of Search ......................................... 556/460

[56] References Cited

U.S. PATENT DOCUMENTS

| | | | |
|---|---|---|---|
| 2,769,829 | 11/1956 | Dobay | 556/460 |
| 2,911,427 | 11/1959 | Brown | 556/460 X |
| 3,070,617 | 12/1962 | Holbrook | 556/460 |
| 3,627,805 | 12/1971 | Thomas et al. | 556/460 |
| 3,983,148 | 9/1976 | Reedy et al. | 556/460 |

OTHER PUBLICATIONS

Noll, "Chemistry and Technology of Silicones", Academic Press, N.Y., (1968), pp. 192-193.

*Primary Examiner*—Paul F. Shaver
*Attorney, Agent, or Firm*—William A. Teoli; James C. Davis, Jr.; James Magee, Jr.

[57] ABSTRACT

A method is provided for hydrolyzing organochlorosilanes using concentrated or saturated aqueous hydrogen chloride solution as the source of water. There is employed a ratio of about 10 to about 30 moles of water per mole of organochlorosilane. In addition to recovering gaseous hydrogen chloride without distillation of aqueous hydrogen chloride solution, the organopolysiloxane hydrolyzate in the form of linear and cyclic siloxanes has reduced total chloride content in the form of dissolved hydrogen chloride and chlorine-terminated linear siloxanes.

5 Claims, 1 Drawing Figure

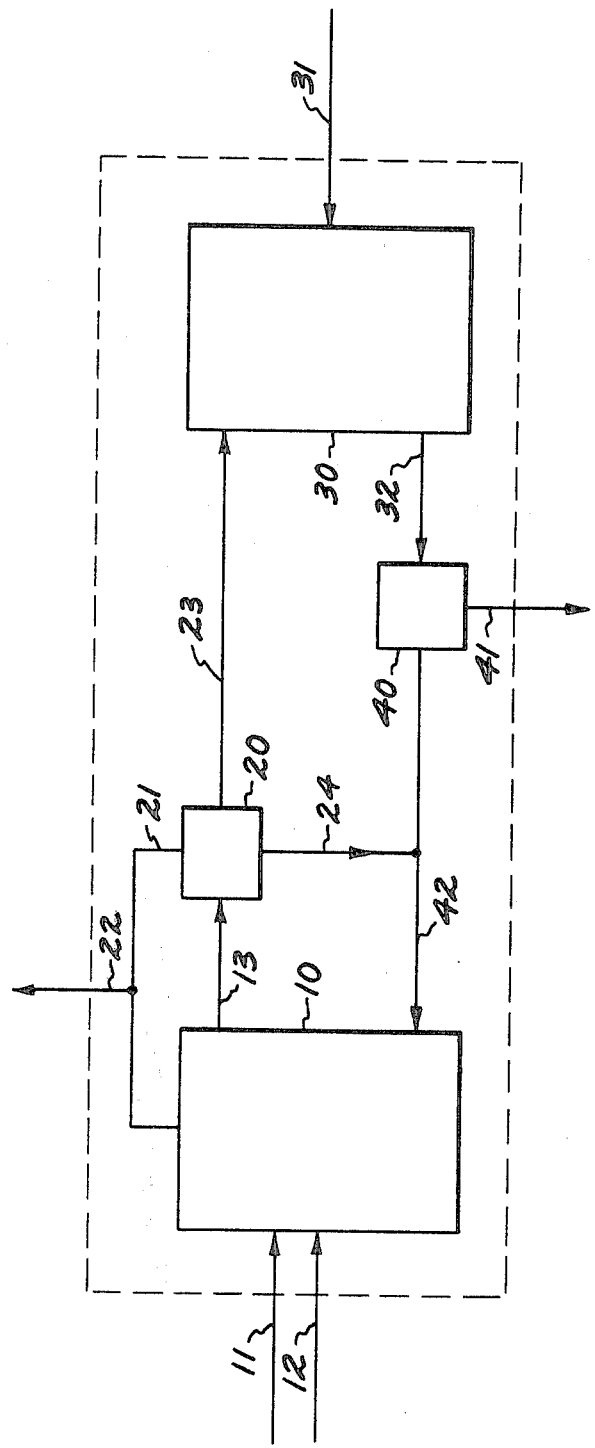

METHOD OF HYDROLYZING ORGANOCHLOROSILANES

CROSS REFERENCE TO RELATED APPLICATIONS

Reference is made to my copending application Ser. No. 244,402, filed Mar. 16, 1981 now abandoned and copending application Ser. No. 330,347, of Abraham Hajjar, Filed Dec. 14, 1981, where both applications are assigned to the same assignee as the present invention.

BACKGROUND OF THE INVENTION

As taught in my copending application Ser. No. 244,402, improved results can be achieved with respect to recovering hydrogen chloride from any organochlorosilane hydrolysis mixture by using a substantially stoichiometric equivalence of water to hydrolyze the organochlorosilane. Further benefits can be obtained if the aqueous hydrolysis product free of the organopolysiloxane hydrolyzate is recycled as the aqueous hydrolysis medium.

Experience has shown, however, that if the aqueous water feed is continuously recycled after it has been separated from the organopolysiloxane hydrolyzate and reused as the source of water which automatically increases the acidity of the hydrolysis medium, the chloride content, i.e. chemically combined or dissolved chloride, of the resulting organopolysiloxane hydrolyzate also substantially increases. In addition, the yields of cyclic organopolysiloxanes are reduced. The buildup of —SiCl end groups and dissolved HCl result in loss of organopolysiloxane hydrolyzate and chlorine in the form of HCl and requires additional process steps to minimize such losses. For example, neutralization of dissolved or chemically combined chloride in the organopolysiloxane hydrolyzate to reduce its acidity results in a loss of chloride values.

As used hereinafter, the expression "WT% total chloride" means total titrated chloride in the organopolysiloxane hydrolyzate either as dissolved HCl or as chloride attached to silicon as terminal —SiCl groups.

The present invention is based on my discovery that if organohalosilanes having the formula,

$$R_{(a)}H_{(b)}SiX_{(4-a-b)}, \quad (1)$$

where R is selected from a $C_{(1-13)}$ monovalent hydrocarbon radical and substituted monovalent hydrocarbon radical, X is a halogen radical, for example chloro, a is an integer equal to 1 to 3 inclusive, b is a whole number equal to 0 to 2 inclusive and the sum of a+b is equal to 3, is hydrolyzed with from about 10 to about 30 moles of water in the form of a concentrated or saturated HX solution at a temperature of from about 0° C. to 60° C., organopolysiloxane hydrolyzate having a higher cyclic siloxane content and also having a reduced weight percent of total halide, based on the weight of organopolysiloxane hydrolyzate can be recovered. For example, within a residence time of 5 minutes in the hydrolysis reactor, the WT% of total chloride obtained by the practice of the method of the present invention will be approximately ½ of the value obtained at the same residence time using substantially stoichiometric amounts of water and organochlorosilane of formula (1).

In addition hydrogen chloride can be recovered directly from the mixture without any requirement of distillation of the aqueous hydrogen chloride solution.

Radicals included within R are, for example, methyl, ethyl, propyl, phenyl, etc., which can be the same or different when a is greater than one.

STATEMENT OF THE INVENTION

In the method of hydrolyzing organohalosilane of formula (1) in a hydrolysis reactor, utilizing a substantially stoichiometric equivalence of organohalosilane and water required for such organohalosilane hydrolysis, resulting in organopolysiloxane hydrolyzate having greater than about 5% by weight, based on the weight of organopolysiloxane hydrolyzate, of halogen radicals in the form of dissolved HX or terminal —SiX groups as a result of the recycling of aqueous HX to the hydrolysis reactor, whereby a loss of halide values results upon the neutralization of the organopolysiloxane hydrolyzate with base, to reduce its acidity, the improvement which comprises, for example, utilizing as the source of water for the organochlorosilane hydrolysis, an aqueous hydrochloric acid solution having at least 35% by weight of hydrogen chloride which is utilized in an amount sufficient to provide a ratio of moles of water to moles of organochlorosilane having a value of from about 10 to about 30, whereby a substantial reduction in the weight percent of halogen radicals, based on the weight of organopolysiloxane hydrolyzate is effected and improved yields of organocyclopolysiloxane is achieved.

In order that those skilled in the art will be better able to practice the invention, reference is made to the drawing. There is shown at 10 a hydrolysis reactor which feeds into a phase separator at 20 and a wash tank or reactor at 30. Another phase separator is shown at 40 which can provide for the recycling of aqueous hydrogen chloride to the aqueous feed. Multiple storage tanks, not shown, may also be used.

More particularly, chlorosilane is introduced into the hydrolysis reactor at 11 and concentrated or saturated HCl solution is introduced into the hydrolysis reactor at 12 at a rate sufficient to maintain a ratio of about 10 to 30 moles of water per mole of chlorosilane at a residence time of 1 to about 30 minutes and preferably 5 to 20 minutes. Preferably, there is used a ratio of about 14 to 22 moles of water, per mole of chlorosilane and temperatures from 0° to about 60° C. Hydrolysis mixture is fed from hydrolysis reactor at 10 through line 13 into phase separator at 20 and anhydrous hydrogen chloride is separated therefrom through lines 21 and 22. In instances where it is desired to maintain anhydrous HCl evolution at a positive pressure, the reactor can be maintained at a pressure of from atmospheric to 200 psi. Organopolysiloxane hydrolyzate is fed from the phase separator at 20 via line 23 into a wash tank or reactor at 30. Hydrolyzate is fed from wash tank 30 through line 32 into another phase separator 40 and low chloride hydrolyzate is separated from the phase separator 40 through line 41. Water or a dilute HCl solution is fed into the wash tank at 31. Recycled concentrated or saturated hydrochloric acid is fed from lines 24 and 42, from the phase separators, back to the hydrolysis reactor 10 at a rate sufficient to maintain the ratio of about 10 to about 30 moles of water per mole of organochlorosilane.

In order that those skilled in the art will be better able to practice the present invention, the following examples are given by way of illustration and not by way of limitation. All parts are by weight.

EXAMPLE 1

Dimethyldichlorosilane and an aqueous solution of hydrogen chloride were fed into a continuous hydrolysis reactor. The resulting hydrolysis mixture was then fed into a phase separator to effect the separation of the polydimethylsiloxane hydrolyzate and hydrochloric acid supersaturated with hydrogen chloride. Hydrogen chloride gas was also evolved directly from the hydrolysis reactor and phase separator. In particular instances, the polydimethylsiloxane was fed into a wash tank to reduce its level of residual chloride, based on the presence of dissolved HCl and polydimethylsiloxane having terminal silicon chloride siloxy units. In addition to the recovery of washed, substantially chloride-free polydimethylsiloxane hydrolyzate in the form of a mixture of mainly silanol terminated polydimethylsiloxanes and low molecular weight cyclic siloxanes, in particular, octamethylcyclotetrasiloxane, concentrated or saturated HCl was recycled from the phase separators back to the hydrolysis reactor.

A series of runs were made following the above-described procedure at dimethyldichlorosilane hydrolysis temperatures of from 9° C. to 61° C. utilizing water to hydrolyze the dimethyldichlorosilane having from 0 to 40.0 weight percent hydrogen chloride and resulting in an aqueous product of about 37 to 45 weight percent HCl. The mole ratio of water to dimethyldichlorosilane in the hydrolysis reactor varied from 2.0 to 32.0 moles of water per mole of dimethyldichlorosilane. The residence time in the hydrolysis reactor wherein the mixture of dimethyldichlorosilane and water or hydrochloric acid was agitated, was from 3.0 minutes to 21.0 minutes. There was obtained as reaction products HCl gas and dimethylpolysiloxane hydrolyzate. In addition, the weight percent of total chloride was also measured. The following results were obtained, where Di is dimethyldichlorosilane and cyclics is total polydimethylcyclopolysiloxane:

| Temp. (°C.) | % HCl In | % HCl Out | H$_2$O/Di (Molar ratio) | Residence Time (Min) | % HCl Gas Evolved | Hydrolyzate Composition (wt %) | | | |
|---|---|---|---|---|---|---|---|---|---|
| | | | | | | D$_4$ | Cyclics | Chloro-End Groups | Total Chloride |
| 61 | 0 | 37.5 | 2.0 | 13.6 | 80.3 | 38.0 | 48.9 | 0.0 | 2.6 |
| 62 | 0 | 37.1 | 4.0 | 3.3 | 54.4 | 38.8 | 51.0 | 0.3 | 2.9 |
| 20 | 0 | 40.9 | 2.0 | 4.1 | 72 | 36.7 | 49.6 | 7.8 | 8.3 |
| 9 | 20 | 41.2 | 2.3 | 5.4 | 81.1 | 35.1 | 53.8 | 11.1 | 8.8 |
| 23 | 37 | 40.7 | 2.0 | 2.2 | 86.1 | 34.3 | 50.2 | 11.0 | 29.9 |
| 26.0 | 37 | 40.7 | 4.0 | 21.0 | 92.1 | 36.9 | 49.6 | 2.8 | 4.7 |
| 13.0 | 37.6 | 41.4 | 3.8 | 18.5 | 93.6 | 31.0 | 43.9 | 5.5 | 6.0 |
| 15 | 37.6 | 41.6 | 2.4 | 3.7 | 98.4 | 34.1 | 45.1 | 12.4 | 11.5 |
| 9 | 38.4 | 41.3 | 3.7 | 5.1 | 90 | 34.2 | 47.2 | 11.1 | 10 |
| 24 | 37.6 | 41.1 | 16.1 | 4.1 | 63.5 | 43.5 | 53.6 | 0.8 | 4.6 |
| 23 | 37 | 40 | 28.3 | 2.8 | 40.3 | 42.0 | 54.8 | 3.6 | 5.4 |
| 17 | 38.9 | 40.2 | 14.3 | 9.9 | 95 | 44.0 | 56.4 | 5.7 | 7.1 |
| 9 | 39.8 | 44.0 | 31.8 | 7.3 | 51.0 | 40 | 53 | 6.3 | 6.7 |
| 26.0 | 37.2 | 40.9 | 19.9 | 10.6 | 64.7 | 37 | 49.6 | 2.4 | 3.5 |

The above results show that for a given residence time, a hydrolysis mixture having mole ratio of about 16 to about 30 moles of water per mole of dimethyldichlorosilane provide organopolysiloxane hydrolyzate having a significant reduction in weight percent total chloride particularly in the form of organopolysiloxane hydrolyzate having terminal chloro substituted siloxy groups. Enhanced anhydrous HCl generation is also achieved along with a significantly improved octamethylcyclotetrasiloxane, D$_4$ production.

EXAMPLE 2

A methylpolysiloxane hydrolyzate was obtained in accordance with the procedure of Example 1 employing a reactor temperature of about 14° C., a residence time of about 5 minutes and a mole ratio of about 19 mole of water per mole of dimethyldichlorosilane using a 40.9% by weight of HCl solution. The resulting methylpolysiloxane hydrolyzate contained about 6.8% of total chloride which was based on the titration of the hydrolyzate with a 1 N-potassium hydroxide solution in methanol which showed the total weight of dissolved HCl plus chemically combined chlorine attached to silicon atoms. In addition, the methylpolysiloxane hydrolyzate was found to have 6.8 weight percent based on the weight of the methylpolysiloxane hydrolyzate of chloro-terminated linear polydimethylsiloxane of which hexamethyl-1,5-dichlorotrisiloxane and octamethyl-1,7-dichlorotetrasiloxane were the major constituents. In addition, the total weight of methylcyclopolysiloxane in the methylpolysiloxane hydrolyzate was found to be about 44.1 weight percent based on gas chromatography, of which there was 34.6 weight percent of octamethylcyclotetrasiloxane.

Portions of the above methylpolysiloxane hydrolyzate were washed with varying amounts of water and 20% hydrochloric acid solutions in a stirred tank for periods of about 5 minutes. After separation of the two liquid phases, the chloride contents of the aqueous and the methylpolysiloxane hydrolyzate phases, and the composition of the methylpolysiloxane hydrolyzate were determined.

It was found that there was a substantial reduction in the weight percent of total chloride. In addition, the resulting methylpolysiloxane hydrolyzate was found to have an increase in weight percent of methylcyclopolysiloxane. For example, with water and a methypolysiloxane hydrolyzate-water volume phase ratio of about 1:2, a methylpolysiloxane hydrolyzate was obtained having 300 ppm of total chloride, 40% by weight of octamethylcyclotetrasiloxane and 52% by weight of methylcyclopolysiloxane. Based on these results, those skilled in the art would know that the wash step in accordance with the practice of the present invention can provide a substantial reduction in the total weight percent of chloride in the methylpolysiloxane hydrolyzate while also increasing the weight percent of methylcyclopolysiloxane.

Although the above examples are directed to only a few of the very many variables present in the practice of the process of the present invention it should be understood that the present invention is directed to a much broader variety of organohalosilanes as shown by formula (1) as well as the molar ratios of reactants, temperatures, pressures and residence times, etc., which are shown in the description preceding these examples.

What I claim as new and desire to secure by Letters Patent of the United States is:

1. In the method of hydrolyzing organochlorosilane of the formula

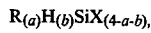

$$R_{(a)}H_{(b)}SiX_{(4-a-b)},$$

in a hydrolysis reactor, where R is selected from $C_{(1-13)}$ monovalent hydrocarbon radicals and substituted monovalent hydrocarbon radicals and X is a halogen radical, utilizing a substantially stoichiometric equivalent of organohalosilane and water required for such organohalosilane hydrolysis, resulting in organopolysiloxane hydrolyzate having greater than about 5% by weight, based on the weight of organopolysiloxane hydrolyzate, of halogen radicals in the form of dissolved HX or terminal—SiX groups as a result of the recycling of aqueous HX to the hydrolysis reactor, whereby a loss of halide values results upon the neutralization of the organopolysiloxane hydrolyzate with base, to reduce its acidity, the improvement which comprises, utilizing as the source of water for the organochlorosilane hydrolysis, an aqueous hydrochloric acid solution having at least 35% by weight of hydrogen chloride which is utilized in an amount sufficient to provide a ratio of moles of water to moles of organochlorosilane having a value of from about 10 to about 30, whereby a substantial reduction in the weight percent of chemically combined halogen radicals, based on the weight of organopolysiloxane hydrolyzate is effected and improved yields of organocyclopolysiloxane is achieved.

2. A method in accordance with claim 1, where there is utilized a ratio of from about 14 to 22 moles of water per mole of organohalosilane in the hydrolysis mixture.

3. A method in accordance with claim 1, where the organohalosilane is dimethyldichlorosilane.

4. A method in accordance with claim 1, where the organohalosiloxane hydrolyzate is further washed or reacted with water or a dilute HX stream prior to recovery to further eliminate chemically combined—SiX groups and dissolved HX, where X is a halogen radical.

5. A method in accordance with claim 1, where reaction temperature is maintained at 0° to 60° C. and residence time of up to about 20 minutes, and pressures of up to 200 psig are employed.

* * * * *